US010113797B2

(12) United States Patent
Dern

(10) Patent No.: US 10,113,797 B2
(45) Date of Patent: Oct. 30, 2018

(54) ENERGY RECOVERY IN A FREEZE-DRYING SYSTEM

(71) Applicant: SP Industries, Inc., Warminster, PA (US)

(72) Inventor: Charles D. Dern, Doylestown, PA (US)

(73) Assignee: SP Industries, Inc., Doylestown, PA (US)

( * ) Notice: Subject to any disclaimer, the term of this patent is extended or adjusted under 35 U.S.C. 154(b) by 0 days.

(21) Appl. No.: 15/260,539

(22) Filed: Sep. 9, 2016

(65) Prior Publication Data

US 2018/0073806 A1 Mar. 15, 2018

(51) Int. Cl.
| | | |
|---|---|---|
| *F26B 23/00* | (2006.01) | |
| *F25B 13/00* | (2006.01) | |
| *F26B 5/06* | (2006.01) | |
| *F26B 9/06* | (2006.01) | |
| *A23F 5/32* | (2006.01) | |
| *A23L 3/44* | (2006.01) | |
| *A61K 9/19* | (2006.01) | |

(52) U.S. Cl.
CPC .............. *F26B 23/001* (2013.01); *A23F 5/32* (2013.01); *A23L 3/44* (2013.01); *A61K 9/19* (2013.01); *F25B 13/00* (2013.01); *F26B 5/06* (2013.01); *F26B 9/066* (2013.01)

(58) Field of Classification Search
CPC .......... F26B 23/001; F26B 13/00; F26B 5/06; F26B 9/066
USPC ...................................... 34/284, 92
See application file for complete search history.

(56) References Cited

U.S. PATENT DOCUMENTS

| | | | |
|---|---|---|---|
| 3,146,077 A | 8/1964 | Fuentevilla | |
| 3,564,727 A | 2/1971 | Fraser | |
| 3,621,587 A | 11/1971 | Smith | |
| 4,016,657 A | 4/1977 | Passey | |
| 4,033,406 A | 7/1977 | Basiulis | |
| 4,081,914 A | 4/1978 | Runtenbach et al. | |
| 4,235,281 A | 11/1980 | Fitch et al. | |
| 4,407,140 A | 10/1983 | Kobayashi | |

(Continued)

FOREIGN PATENT DOCUMENTS

| | | |
|---|---|---|
| CN | 201706847 | 1/2011 |
| CN | 202126133 U | 1/2012 |

(Continued)

OTHER PUBLICATIONS

Muhammad Idrus Alhamid et al., "Characteristics of Vacuum Freeze Drying with Utilization of Internal Cooling and Condenser Waste Heat for Sublimation" Makara Seri Teknologi, 2013, 17(2): 51-58.

(Continued)

*Primary Examiner* — Stephen M Gravini
(74) *Attorney, Agent, or Firm* — Lowenstein Sandler LLP

(57) ABSTRACT

Disclosed herein are embodiments of an energy recovery system for a freeze-drying system. In some embodiments, the freeze-drying system includes a freeze dryer chamber having one or more shelves disposed therein; a refrigeration system comprising a refrigerant condenser; a heat exchanger; a first fluid line to thermally couple the refrigerant condenser to the heat exchanger; and a second fluid line to thermally couple the one or more shelves to the heat exchanger.

18 Claims, 9 Drawing Sheets

(56) References Cited

U.S. PATENT DOCUMENTS

| | | | | |
|---|---|---|---|---|
| 4,449,305 | A * | 5/1984 | Baron | F26B 5/06 34/92 |
| 4,547,977 | A * | 10/1985 | Tenedini | F26B 5/06 165/65 |
| 4,784,216 | A | 11/1988 | Bracegirdle et al. | |
| 5,743,023 | A * | 4/1998 | Fay | F25D 31/005 34/287 |
| 5,937,536 | A * | 8/1999 | Kieselbach | F26B 5/044 34/202 |
| 6,220,048 | B1 | 4/2001 | Finan, Sr. et al. | |
| 6,233,841 | B1 | 5/2001 | Beach | |
| 6,303,080 | B1 | 10/2001 | Tuma | |
| 6,935,049 | B2 * | 8/2005 | Alstat | C02F 1/22 34/288 |
| 7,347,004 | B1 * | 3/2008 | Halvorsen | F26B 5/06 34/73 |
| 8,528,225 | B2 * | 9/2013 | Weisselberg | F26B 5/00 201/27 |
| 8,919,007 | B2 * | 12/2014 | Friess | F26B 5/06 250/231.1 |
| 8,938,979 | B2 | 1/2015 | Cheng | |
| 8,966,782 | B2 * | 3/2015 | Kuu | F26B 5/06 34/287 |
| 9,052,138 | B2 * | 6/2015 | DeMarco | F26B 5/065 |
| 9,200,836 | B2 * | 12/2015 | Gasteyer, III | F26B 5/06 |
| 9,739,532 | B2 * | 8/2017 | Baugh | F26B 5/06 |
| 2002/0050072 | A1 * | 5/2002 | Akimoto | F26B 5/06 34/92 |
| 2012/0009085 | A1 * | 1/2012 | Burger | A61L 2/206 422/33 |

FOREIGN PATENT DOCUMENTS

| | | |
|---|---|---|
| CN | 102506572 A | 6/2012 |
| DE | 20008915 | 6/2001 |
| FR | 2911672 | 7/2008 |

OTHER PUBLICATIONS

International Search Report and Written Opinion for International Application No. PCT/US2017/050705 dated Jul. 12, 2017, 10 pages.

* cited by examiner

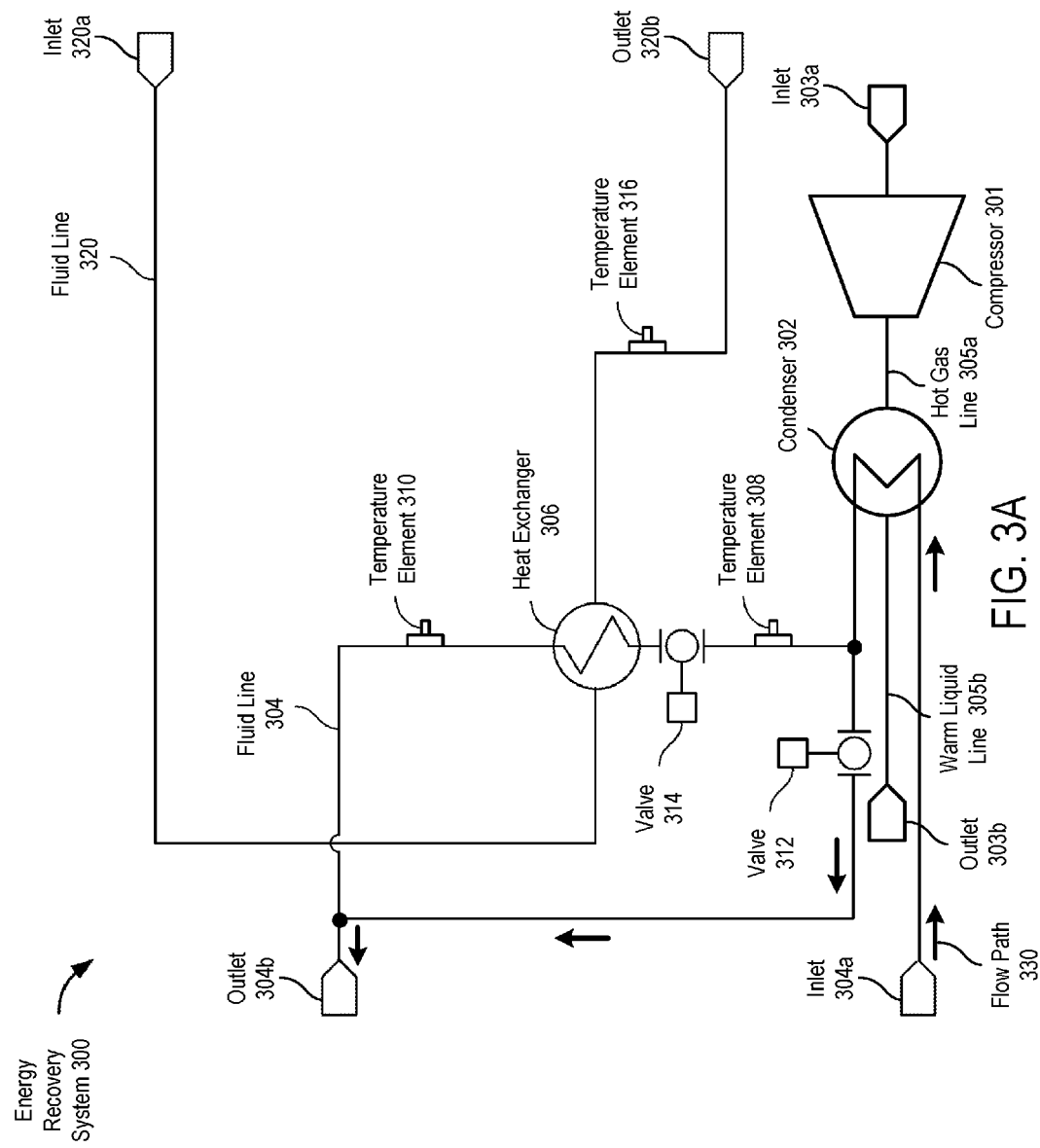

ENERGY RECOVERY IN A FREEZE-DRYING SYSTEM

FIELD OF THE INVENTION

The present disclosure relates to field of freeze-drying systems, and more particularly, to energy recovery in freeze-drying systems.

BACKGROUND

Freeze-drying (e.g., lyophilization, cryodesiccation) is a process to remove water and/or other solvents from products. Freeze-drying has many applications such as preserving a perishable material, making a material more convenient for transport, making of ceramics, producing a product that has a short reconstitution time with acceptable potency levels, and so forth. Freeze-drying can be used for many different materials, including, but not limited to, food, pharmaceuticals, and biological specimens.

In a typical freeze-drying process, the sample, or vials or containers containing the sample, are loaded on temperature-controlled shelves within a chamber and cooled to low temperatures until completely solidified. The freeze-drying chamber pressure is then reduced and the shelf temperature is adjusted to enable removal of the frozen solvent (i.e., drying) via sublimation in a step referred to as "primary drying." When sublimation is complete, the shelf temperature is raised during a "secondary drying" step to remove additional un-frozen solvent bound to the solid product by e.g. adsorption. When sufficient solvent is removed, the drying process is concluded. If the sample was contained in vials or containers, the vials or containers are then sealed, typically under a sub-ambient pressure of inert gas.

BRIEF DESCRIPTION OF THE DRAWINGS

The present disclosure is illustrated by way of example, and not by way of limitation, in the figures of the accompanying drawings.

FIG. 3A is a schematic view of a third embodiment of an energy recovery system for a freeze-drying system depicting a first fluid flow path.

DETAILED DESCRIPTION OF THE INVENTION

The freeze-drying process includes at least a freezing stage, a primary drying (e.g., sublimation) stage, and a secondary drying (e.g., desorption) stage. During the freezing stage, a product is frozen and ice crystals are formed in the product. During the primary drying stage, water is removed from the product via sublimation of the free ice crystals by an increase in temperature. During the secondary drying stage, the temperature is raised higher to remove bound water molecules from the product.

Freeze-drying can be expensive, time-consuming, and energy-demanding. The primary drying stage, for example, may be slow (in some instances taking multiple days to complete) and may take longer to complete than any of the other stages.

A refrigeration unit having one or more mechanical compressor(s) can be used to cool the freeze-drying chamber. At later stages of the process, the compressor(s) may be used to cool the freeze dryer ice condenser and waste heat of the compressor(s) is rejected out of the system, while at the same time heat is placed into the shelves of the chamber by other means such as an electric heater.

The embodiments of the present disclosure relate to a system and method for energy recovery within a freeze-drying system. Specifically, the embodiments allow for waste heat generated by a mechanical refrigeration compressor to be reclaimed and utilized to heat product shelves within a chamber of the freeze-drying system. Unlike traditional freeze-drying systems that only use electrical heating devices to heat the shelves, the present embodiments thermally couple the condenser to the shelves, which drives down the energy requirements of the system.

In certain embodiments, the waste heat from the condenser may be supplied to the shelf when a temperature of the condenser, or fluid exiting the condenser, is within a particular range. A processing device, for example, of a programmable logic controller or a flow controller, may execute a recipe that causes the heat to be transferred from the freeze dryer condenser to the shelves when the shelf temperature is in range (e.g., within −25° C. to 35° C.), and then stops the heat transfer when the temperature is not within the range or if the shelves have reached a target temperature.

Figure 1:
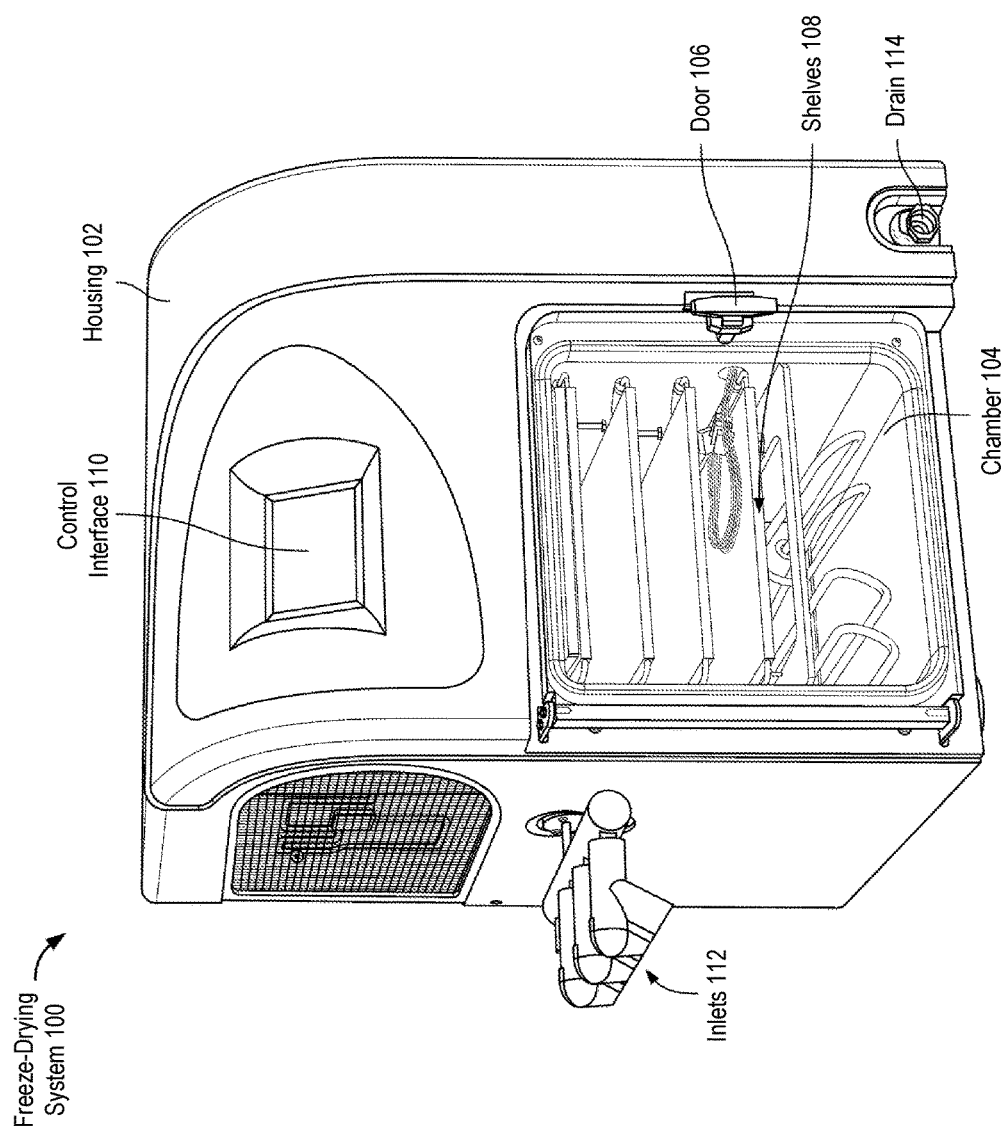
FIG. 1 is a depiction of a freeze-drying system in accordance with embodiments of the present disclosure.

FIG. 1 is a depiction of a freeze-drying system 100 in accordance with embodiments of the present disclosure. The freeze-drying system 100 may perform freeze-drying of a product. The freeze-drying process may include multiple stages (e.g., a freezing stage, a primary drying stage, a secondary stage, etc.). The freeze-drying system 100 may include a housing 102 that encloses various components of the freeze-drying system 100, such as a chamber 104 for loading samples, a refrigeration unit, fluid lines, gas lines, etc. The chamber 104 may be accessible via a door 106 that can seal the chamber 104 and sustain vacuum conditions within the chamber 104. The chamber 104 may include one or more shelves 108 disposed thereon, which may be used for securing samples. One or more inlets 112 may facilitate gas flow and/or vacuum attachments to control, respectively, gas flow into the chamber 104 and vacuum conditions within the chamber 104. A drain 114 may be used to remove excess water from the chamber, for example, resulting from ice formation.

In certain embodiments, the freeze-drying system 100 may be adapted to perform steam sterilization cycles. The freeze-drying system 100 may perform a clean-in-place (CIP) and/or a steam sterilization cycle after each use of the freeze-drying system 100 to ensure that a product is not contaminated by material previously lyophilized in the freeze-drying system 100. For example, in certain embodiments, the freeze-drying system 100 may include one or more inlets for the purposes of introducing cleaning media and/or steam into a chamber of the system. In certain embodiments, the chamber 104 and shelves 108 may be replaced with a manifold with attached flasks.

In certain embodiments, the chamber 102 may include one or more orifices for connecting various valves and gauges. For example, a gauge, such as a Pirani gauge, may be coupled to the chamber to measure pressure within the chamber 102.

In some embodiments, the shelves 108 may be thermally coupled to a heating element for temperature control. In some embodiments, the heating element may be an electric heating device. In some embodiments, the heating element may be one or more fluid lines that are thermally coupled the shelves 108, which may regulate heat delivered to the shelves by fluid flow through the one or more fluid lines.

In certain embodiments, the freeze-drying system 100 may include an internal condenser, which may be contained within the housing 102. In other embodiments, the freeze-drying system 100 may include an external condenser. In such embodiments, the depressurization orifices may be disposed proximate the chamber 104, a separate condensing chamber, or a conduit connecting the chamber 104 to the condensing chamber. If the orifices are on the condensing chamber or in the conduit between the isolation valve and the condensing chamber, then the isolation valve separating the chamber 104 and the condensing chamber will be opened to achieve identical pressures between the two. In some embodiments, more than one chamber 104 may be connected to a single condensing chamber and vice versa.

In some embodiments, the freeze-drying system 100 includes a control interface 110, which may allow a user to program a recipe and cause the recipe to be executed. The freeze-drying system 100 includes various control hardware (e.g., one or more processing devices) and software systems adapted to command and coordinate the various elements of the freeze-drying system 100, and carry out the pre-programmed freeze-drying cycle. The various control hardware and software systems may also provide documentation, data logging, alarms, and system security capabilities as well. In addition, auxiliary systems to the freeze-dryer system may include a leak check system, performance check system, and various subsystems to clean and sterilize the product chamber and/or auto-load/unload the product in the product chamber, as well as associated mechanical or cryogenic refrigeration system accessories such as refrigeration skids, compressors, condensers, heat exchangers, heat transfer fluid systems, pumps, heaters, expansion tanks, cryogen tanks, piping, valves, sensors, etc.

After freezing of the sample is complete, drying steps are initiated which include a primary drying step and secondary drying step. Primary drying involves activating a vacuum pump and condenser refrigeration system to establish the desired sublimation and condensing conditions in the chamber 104. In some embodiments, a small bleed flow of a gas (e.g., an inert gas) into the chamber throughout the drying process to help control the vacuum level. After the vacuum pressure conditions are attained, the shelves 108 are warmed (e.g., using waste heat from the condenser, as will be discussed in more detail below) to the desired primary drying temperature, which is dictated by the thermal and mechanical properties of the material undergoing freeze-drying. Primary drying is completed when all the unbound water has been removed by sublimation, as determined by one or more of product temperature measurements, humidity measurements, comparison of capacitance manometer and Pirani gauge measurements, analysis of samples obtained with a sample thief, or other techniques. Once primary drying is complete, the freeze-dryer shelf temperatures are further warmed at a desired warming rate until the product or materials reach a temperature when desorption of bound water may be adequately achieved. This final product temperature depends on product composition and could be about 20° C. or higher. After drying is complete, the product or material is removed from the chamber 104. At any time during the process, the freeze-drying system 100 may be capable of emergency stop or shutdown, which would close the pressurization and depressurization control valves while the chamber remains under vacuum.

FIGS. 2A-2D are schematic views of a first embodiment of an energy recovery system 200 for a freeze-drying system (e.g., freeze-drying system 100). The energy recovery system 200 includes a compressor 201, a refrigerant condenser 202, a fluid line 204, and a heat exchanger 206 disposed along the fluid line 204. The refrigerant condenser 202 may be part of a refrigeration unit of the freeze-drying system. The compressor 201 receives a refrigerant gas via inlet 203a from a process condenser (which may be internal to a chamber of the freeze-drying system, or external to the chamber of the freeze-drying system and connected to the chamber via a port) or other heat exchanger, and discharges the refrigerant as a hot gas via hot gas line 205a into the refrigerant condenser 202. The refrigerant condenser 202 condenses the hot gas refrigerant into a warm liquid, which exits through warm liquid line 205b and back to the process condenser via outlet 203b.

Figure 2A:
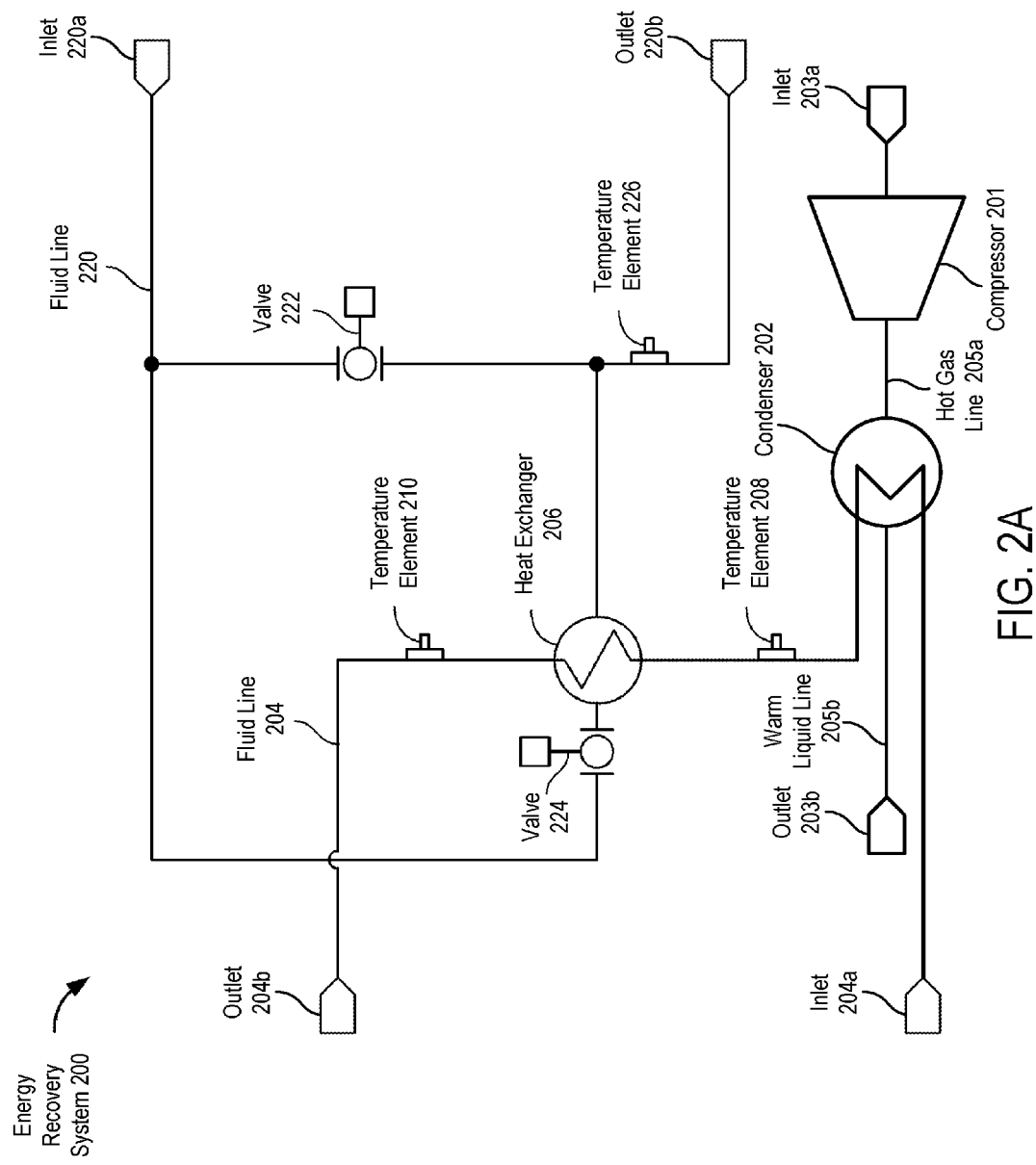
FIG. 2A is a schematic view of a first embodiment of an energy recovery system for a freeze-drying system.
Figure 2B:
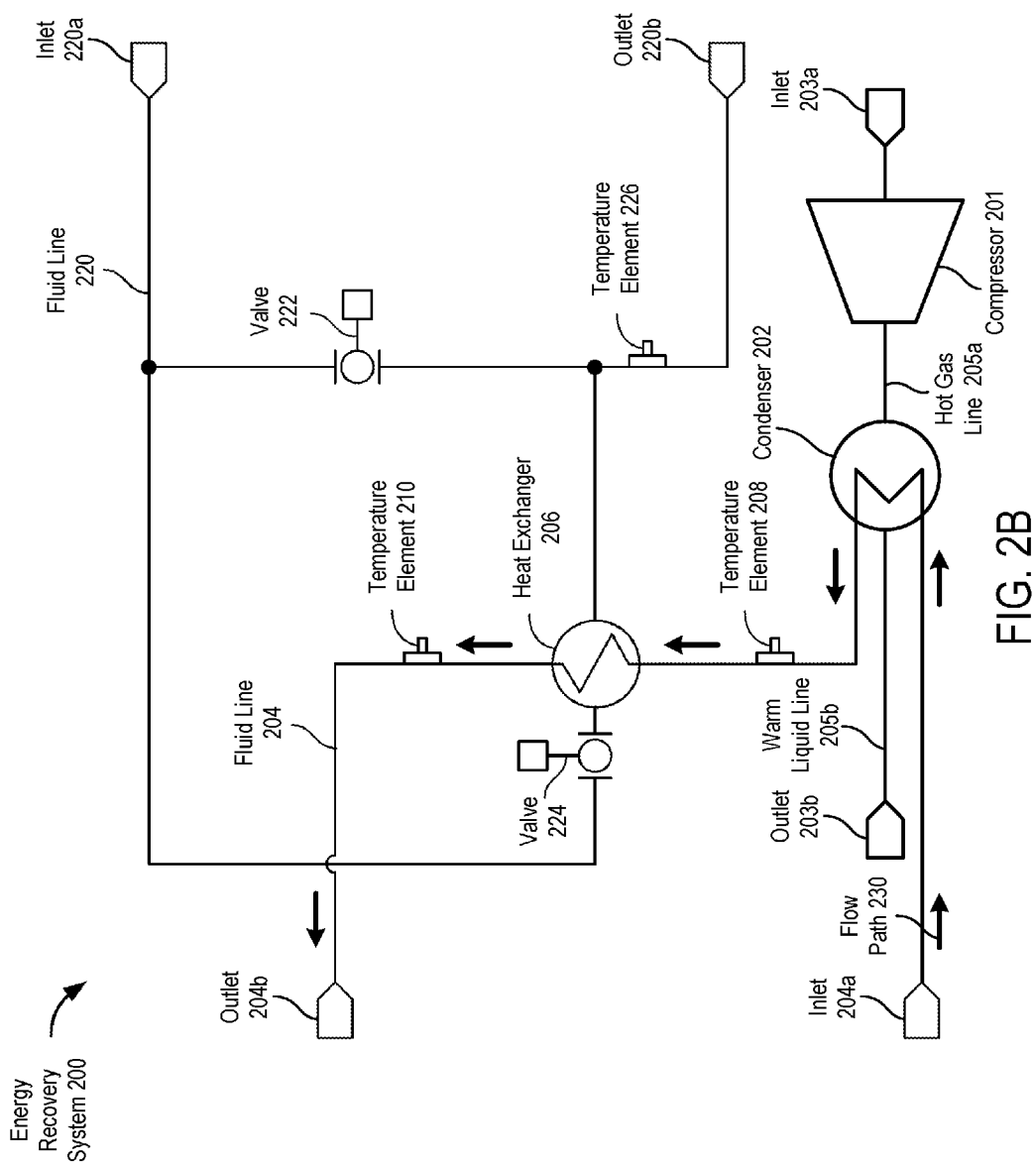
FIG. 2B is a schematic view of a first embodiment of an energy recovery system for a freeze-drying system depicting a first fluid flow path.

The fluid line 204 may supply water (or another type of cooling medium) to the refrigerant condenser 202 via inlet 204a to remove heat from the refrigerant condenser 202. The water is then directed through the heat exchanger 206, and may return to a separate tower or other cooling system of the freeze-drying system via outlet 204b. In such embodiments, the water may be continuously cycled back through the fluid line 204. In other embodiments, fresh water may be cycled through the fluid line 204, and the return water may be disposed of. In some embodiments, water-glycol fluid may be used by the cooling system. In some embodiments, one or more temperature elements, such as temperature elements 208 and 210 (e.g., thermocouples), may be distributed along the fluid line 204. FIG. 2B illustrates a flow path 230 defined by the fluid line 204. Water passes from the water supply through the refrigerant condenser 202, through the heat exchanger 206, and through a water return.

In certain embodiments, the freeze-drying system may be a steam sterilizable freeze-drying system, and the heat exchanger 206 may be a heat exchanger used to cool a heat transfer fluid after steam sterilization. In such embodiments, the heat exchanger 206 may be adapted for the energy recovery system 200 to transfer heat rejected from the refrigerant condenser 202.

The energy recovery system 200 further includes a fluid line 220, which includes valves 222 and 224, and one or more temperature elements, such as temperature element 226. In some embodiments, the fluid line 220 may include additional valves. In some embodiments, the valves 222 and 224 may be located at different locations along the fluid line 220.

The fluid line 220 may pass through one or more shelves (e.g., the shelves 108) and deliver a heat transfer fluid to the shelves. In some embodiments, the heat transfer fluid is continuously cycled through the shelves by flowing out through the outlet 220b and returning through the inlet 220a.

In some embodiments, the heat transfer fluid is aqueous based or oil based. For example, the heat transfer fluid may be a mineral oil.

Figure 2C:
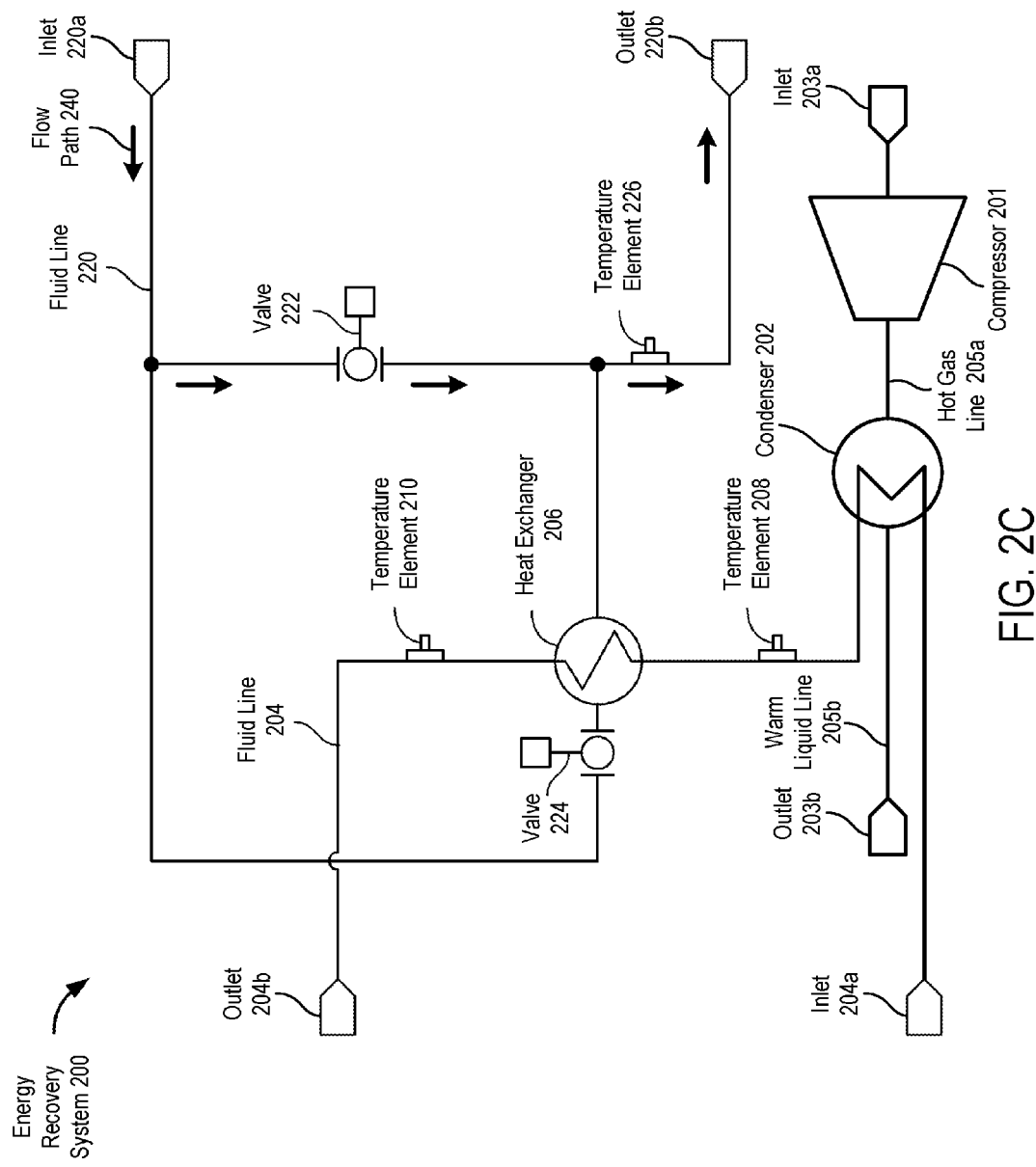
FIG. 2C is a schematic view of a first embodiment of an energy recovery system for a freeze-drying system depicting a second fluid flow path.
Figure 2D:
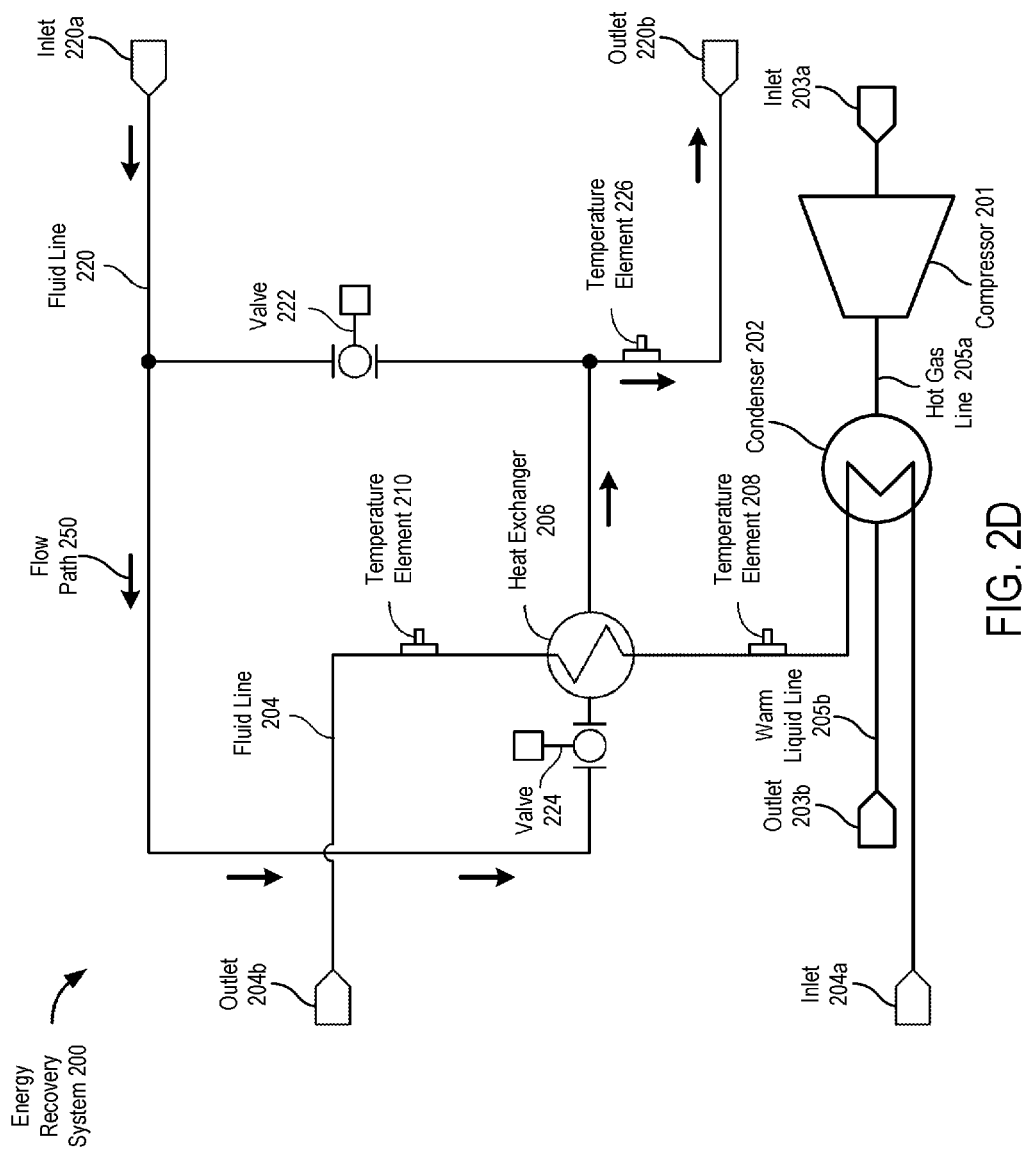
FIG. 2D is a schematic view of a first embodiment of an energy recovery system for a freeze-drying system depicting a third fluid flow path.

The positions (opened, closed, partially opened, or partially closed) of valves 222 and 224 may define a flow path of the heat transfer fluid through the fluid line 220, as illustrated in FIGS. 2C-2D. FIG. 2C illustrates a flow path 240 in which the heat transfer fluid is cycled through the shelves. The flow path 240 results from the valve 222 being opened and the valve 224 being closed. In this scenario, no heat transfer will occur between any fluids in the fluid line 220 and the fluid line 204.

FIG. 2D illustrates a flow path 250 in which the heat transfer fluid is cycled through the shelves and the heat exchanger 206. The flow path 250 results from the valve 222 being closed and the valve 224 being opened. In this scenario, there will be heat transfer between the fluids in the fluid line 220 and the fluid line 204 at the heat exchanger 206, resulting in thermal coupling of the shelves to the condenser 202.

Figure 2E:
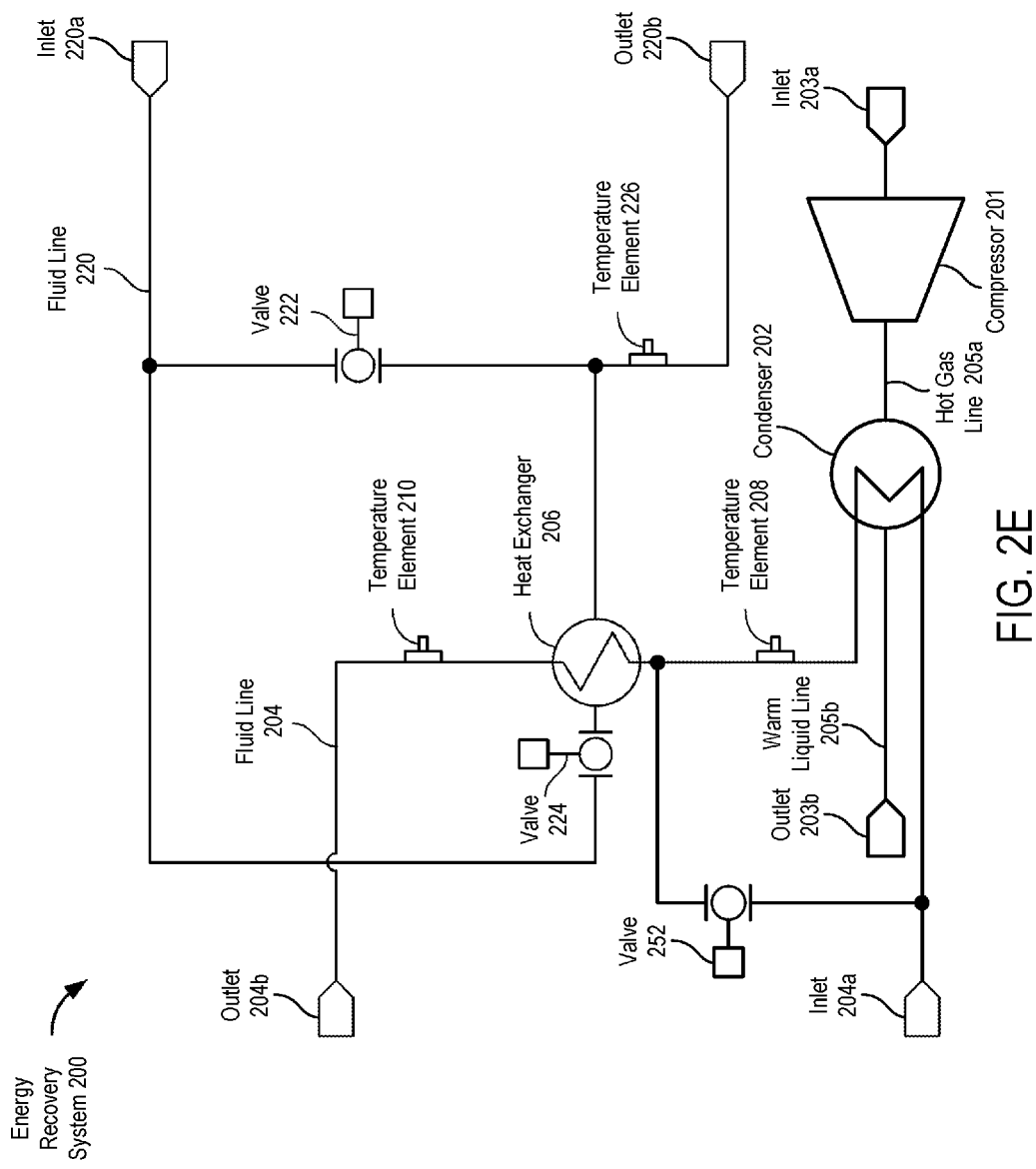
FIG. 2E is a schematic view of a second embodiment of an energy recovery system for a freeze-drying system.

FIG. 2E illustrates a second embodiment of the energy recovery system 200, which includes a valve 252 that may allow for fluid flow to be diverted from refrigerant condenser 202 when the valve 252 is opened (e.g., for a post steam-in-place process).

Figure 3B:
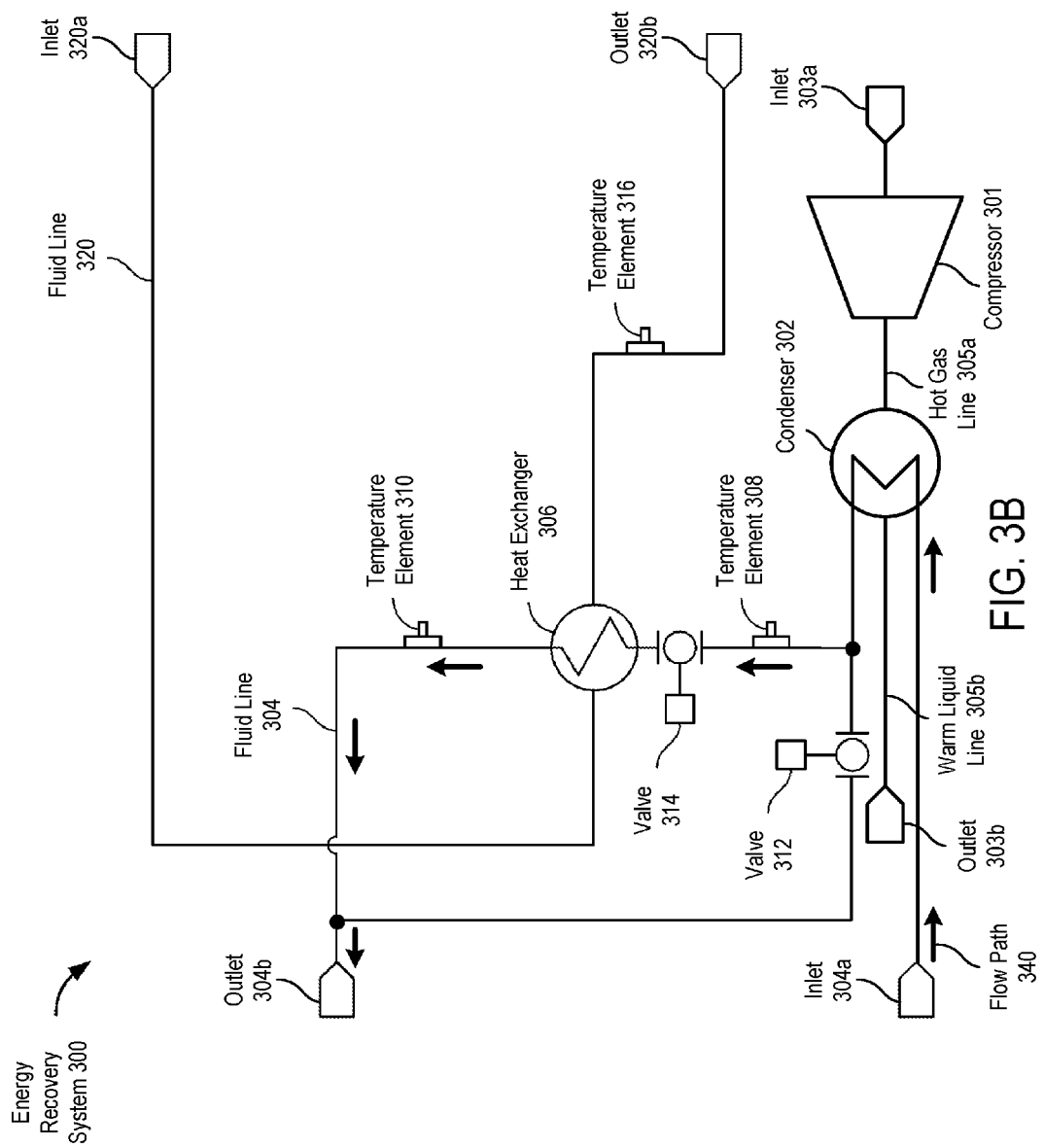
FIG. 3B is a schematic view of a third embodiment of an energy recovery system for a freeze-drying system depicting a second fluid flow path.

FIGS. 3A-3B are schematic views of a third embodiment of an energy recovery system 300 for a freeze-drying system. The energy recovery system 300 includes many of the same or similar components as the energy recovery system 200, including a refrigerant condenser 302, a compressor 301, inlet 303a, outlet 303b, hot gas line 305a, warm liquid line 305b, a heat exchanger 306, temperature elements 308, 310, and 316, inlets 320a and 320b, and outlets 304a and 304b. In the energy recovery system 300, the fluid lines 304 and 320 are arranged differently than fluid lines 204 and 220, respectively, of the energy recovery system 200. Specifically, valves 312 and 314 are included in the fluid line 304 to control the flow of water through the heat exchanger 306. As illustrated in FIG. 3A, a flow path 330 results when the valve 312 is opened and the valve 314 is closed. In this scenario, the heat exchanger 306 is bypassed with no heat transfer occurring between any fluids in the fluid line 320 and the fluid line 330. As illustrated in FIG. 3, a flow path 340 results when the valve 312 is closed and the valve 314 is opened. In this scenario, water passes through both the condenser 302 and the heat exchanger and heat is exchanged between the fluids in the fluid line 320 and 340, resulting in thermal coupling of the shelves to the condenser 302.

Other arrangements of the fluid lines are contemplated, and thus the embodiments described herein are not limited to those disclosed, as would be appreciated by one of ordinary skill in the art.

In certain embodiments, a flow controller may be operatively coupled to one or more components of the energy recovery systems (e.g., any of the energy recovery systems 100 and 200) to regulate the flow rates and flow directions of fluid through any of the fluid lines (e.g., any of the fluid lines 204, 220, 304, or 320), control positions of one or more of the valves (e.g., any of the valves 222, 224, 312, and 314), and measure the temperatures of the temperature elements. In certain embodiments, the flow controller may control, or may be part of a larger control system that controls, other aspects of a freeze-drying system, including, but not limited to, gas flow or vacuum conditions in a chamber and temperature cycles. The flow controller may be a programmable flow controller, in some embodiments, and may be programmed to execute a freeze-drying recipe.

In some embodiments, the flow controller may control the positions of the various valves to regulate the flow paths of fluid through the fluid lines, thus facilitating thermal coupling between the shelves and the condenser. In certain embodiments, the flow controller may determine when to thermally couple the shelves to the condenser, for example, in response to determining that a temperature of water exiting the condenser has reached a particular temperature range. An exemplary method for this functionality is described in greater deal below with respect to FIG. 4.

Figure 4:
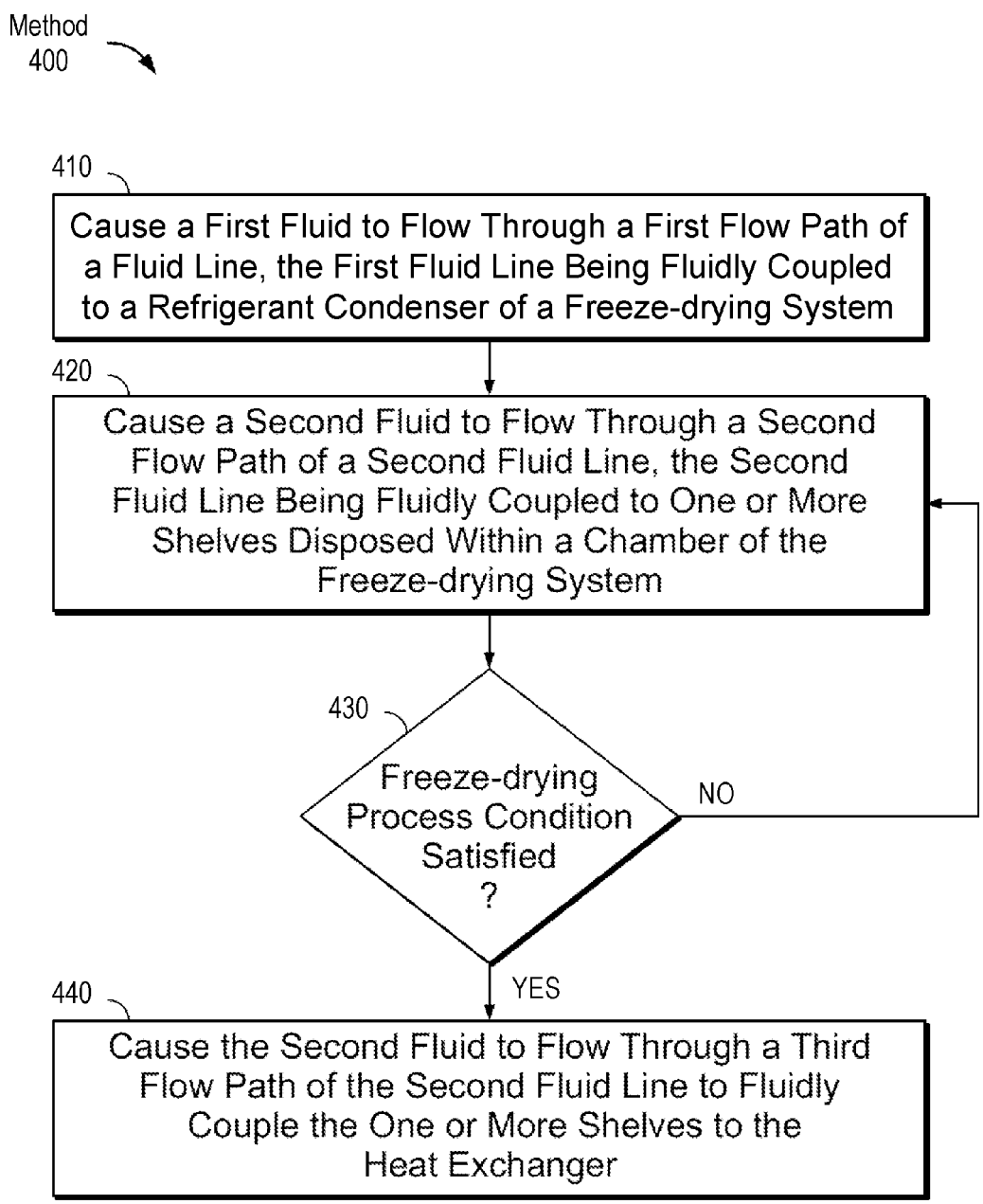
FIG. 4 is a flow diagram illustrating a method for energy recovery in a freeze-drying system in accordance with embodiments of the present disclosure.

FIG. 4 is a flow diagram illustrating a method 400 for energy recovery in a freeze-drying system in accordance with embodiments of the present disclosure. Method 400 may be performed by any of the energy recover systems described herein, such as energy recovery systems 200 and 300. However, it should be understood that method 400 may also be used by other systems, and is limited to neither freeze-drying systems nor energy recovery systems generally. The method 400 may be performed by a processing device (e.g., of a flow controller or other control system/device) implementing processing logic. The processing logic may comprise hardware (e.g., circuitry, dedicated logic, programmable logic, microcode, etc.), software (e.g., instructions run on a processing device to perform hardware simulation), or a combination thereof.

At block 410, the processing device causes a first fluid to flow through a first flow path (e.g., flow path 230) of a fluid line (e.g., fluid line 204), the first fluid line being thermally coupled to a condenser (e.g., refrigerant condenser 202) and a heat exchanger (e.g., 206) of a freeze-drying system (e.g., energy recovery system 200, which may be part of freeze-drying system 100). In some embodiments, the refrigerant condenser 202 is fluidly coupled to a compressor (e.g., compressor 201), which receives a refrigerant from a process condenser or other heat exchanger. The processing device may regulate the flow rate and direction of the first fluid. For example, the processing device may be operatively coupled to a pump system that is fluidly coupled to the first fluid line. In some embodiments, the first fluid may be water, a glycol solution, a non-aqueous coolant, or a heat transfer fluid. In some embodiments, the first fluid may have a temperature from −80° C. to 130° C.

At block 420, the processing device causes a second fluid to flow through a second flow path (e.g., flow path 240) of a second fluid line (e.g., fluid line 220), the second fluid line being thermally coupled to one or more shelves (e.g., 108) shelves disposed within a chamber of the freeze-drying system. The processing device may cause the second fluid to flow through the second flow path by toggling positions of valves within the second fluid line. For example, the processing device may cause a first valve to close or remain closed and a second valve to open or remain opened. In some embodiments, the second fluid is water, a non-aqueous coolant, or a heat transfer fluid.

At block 430, the processing device determines whether a freeze-drying process condition is satisfied. In some embodiments, the condition is a temperature condition. For example, in such embodiments, the processing device may measure one or more temperatures of the first or second fluids at specific points (e.g., using any of temperature elements 210, 208, or 226). In some embodiments, the temperature condition is a condition that a measured temperature is within a pre-defined range, or that the temperature is greater than or equal to a threshold temperature. In some embodiments, the threshold temperature is selected from a temperature ranging from −25° C. to 35° C. (e.g., a 30° C. threshold temperature). In some embodiments, the condition may be satisfied if a measured temperature is in a range of −20° C. to 40° C., or in a range of −25° C. to 35° C. In some embodiments, the temperature condition is satisfied when a temperature of the second fluid (e.g., fluid through fluid line 220) is less than a temperature of the first fluid (e.g., fluid through fluid line 204). In some embodiments, if the condition may be determined to have been satisfied if a temperature of the first fluid exiting the condenser (e.g., as measured by temperature element 208) satisfies the temperature condition. For example, if the temperature of water exiting the refrigerant condenser is greater than 30° C., the processing device may determine that the condition has been satisfied.

In some embodiments, the freeze-drying process condition is the occurrence or execution of a step in a process recipe (such as a pre-defined process recipe). For example, the condition may be the execution of a secondary drying state of the freeze-drying process. In some embodiments, the condition may be user-induced. For example, a user of the freeze-drying system may directly override the recipe and enter a command or toggle a switch that indicates to the processing device that the condition has been satisfied.

If the processing device determines that the freeze-drying process condition is not satisfied, the method 400 then proceeds back to block 420. In this scenario, the second fluid bypasses the heat exchanger, which thermally isolates the first and second fluids, and thus thermally isolates the shelves and the condenser from each other. The method 400 may cycle through blocks 420 and 430 continuously until it is determined that the condition is satisfied, or until another event terminates the method 400.

In some embodiments (e.g., those based on energy recovery system 200 wherein there is full water flow from the refrigeration condenser 202 to the heat exchanger 206), the system may modulate the valves such that no heat transfer fluid flows through the heat exchanger, the system may modulate the valves to allow full heat transfer fluid flow through the heat exchanger, or the system may allow for partial heat transfer fluid flow through the heat exchanger. In such embodiments, the system may modulate the valves depending on desired temperature conditions and process steps. In some embodiments (e.g., those based on energy recovery system 300 wherein there is full heat transfer fluid flow between the heat exchanger 306 and shelves), the system may modulate the valves inverse to the embodiment just described.

If the processing device determines that the freeze-drying process condition is satisfied, the method 400 then proceeds to block 440. At block 440, the processing device causes the second fluid to flow through a third flow path (e.g., flow path 250) of the second fluid line to thermally couple the one or more shelves to the heat exchanger. For example, the processing device may cause the second fluid to flow through the third flow path by causing the first valve to open (which may have been previously closed) and the second valve to close (which may have been previously opened). Flow of the second fluid through the third flow path while the first fluid flows through the first flow path results in heat being transferred from the condenser to the first fluid, from the first fluid to the heat exchanger, from the heat exchanger to the second fluid, and from the second fluid to the shelves, thus thermally coupling the condenser to the shelves.

In some embodiments, the method 400 proceeds back to block 420, for example, if the processing device determines that the freeze-drying process condition is no longer satisfied. In some embodiments, the method 400 may proceed back to the block 420 if the processing device determines that a temperature of the second fluid satisfies a temperature condition (e.g., a temperature of the second fluid, as measured by the temperature element 226, is greater than 20° C.). This may correspond to an indication that the shelf temperature has reached a target temperature.

It should be noted that the above described operations are an exemplary method for operating a freeze-drying system 100 and that, in alternative embodiments, certain ones of the operations of FIG. 4 may be optional or take a simpler form. Moreover, one or more of the blocks of the method 400 may be performed concurrently and in a different order than shown, as would be appreciated by one of ordinary skill in the art.

It will be apparent from the foregoing description that aspects of the present disclosure may be embodied, at least in part, in software. That is, the techniques may be carried out in a computer system or other data processing system in response to a processing device, for example, executing sequences of instructions contained in a memory. In various embodiments, hardware circuitry may be used in combination with software instructions to implement the present disclosure. Thus, the techniques are not limited to any specific combination of hardware circuitry and software or to any particular source for the instructions executed by the data processing system. In addition, throughout this description, various functions and operations may be described as being performed by or caused by software code to simplify description. However, those skilled in the art will recognize what is meant by such expressions is that the functions result from execution of the code by processing device.

A machine-readable medium can be used to store software and data which when executed by a general purpose or special purpose data processing system causes the system to perform various methods of the present disclosure. This executable software and data may be stored in various places including, for example, system memory and storage or any other device that is capable of storing software programs and/or data. Thus, a machine-readable medium includes any mechanism that provides (i.e., stores) information in a form accessible by a machine (e.g., a computer, network device, personal digital assistant, manufacturing tool, any device with a set of one or more processors, etc.). For example, a machine-readable medium includes recordable/non-recordable media such as read only memory (ROM), random access memory (RAM), magnetic disk storage media, optical storage media, flash memory devices, etc.

Unless stated otherwise as apparent from the foregoing discussion, it will be appreciated that terms such as "maintaining," "providing," "determining," "initiating," or the like may refer to the actions and processes of a computer system, or similar electronic computing device, that manipulates and transforms data represented as physical (e.g., electronic) quantities within the computer system's registers and memories into other data similarly represented as physical within the computer system memories or registers or other such information storage or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present disclosure are not described with reference to any particular programming language. It will be appreciated that a variety of programming languages may be used to implement embodiments of the present disclosure.

In the foregoing description, numerous specific details are set forth, such as specific materials, dimensions, processes parameters, etc., to provide a thorough understanding of the embodiments of the present disclosure. The particular features, structures, materials, or characteristics may be combined in any suitable manner in one or more embodiments. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form.

Reference throughout this specification to "an embodiment", "certain embodiments", or "one embodiment" means that a particular feature, structure, or characteristic described in connection with the embodiment is included in at least one embodiment. Thus, the appearances of the phrase "an embodiment", "certain embodiments", or "one embodiment" in various places throughout this specification are not necessarily all referring to the same embodiment, and such references mean "at least one".

It is to be understood that the above description is intended to be illustrative, and not restrictive. Many other embodiments will be apparent to those of skill in the art upon reading and understanding the above description. The scope of the disclosure should, therefore, be determined with reference to the appended claims, along with the full scope of equivalents to which such claims are entitled.

What is claimed is:

1. A freeze-drying system comprising:
    a freeze dryer chamber having one or more shelves disposed therein;
    a refrigeration system comprising a refrigerant condenser;
    a heat exchanger;
    a first fluid line that passes through the refrigerant condenser and the heat exchanger defining a first fluid flow path therebetween, wherein the first fluid line is arranged to thermally couple the refrigerant condenser to the heat exchanger; and
    a second fluid line, separate from the first fluid line, that passes through the one or more shelves and the heat exchanger and is adapted to alternate between a second fluid flow path and a third fluid flow path, wherein the second fluid flow path is defined through the one or more shelves and the heat exchanger, wherein the third fluid flow path is defined through the one or more shelves, and wherein the second fluid line is arranged to thermally couple the one or more shelves to the heat exchanger to facilitate transfer of refrigerant condenser-produced heat to the one or more shelves when the second fluid line defines the second fluid flow path.

2. The freeze-drying system of claim 1, wherein the second fluid line comprises a first valve and a second valve.

3. The freeze-drying system of claim 2, wherein the second fluid line defines the second fluid flow path from the one or more shelves to the heat exchanger when the first valve is open and when the second valve is closed.

4. The freeze-drying system of claim 3, wherein the first fluid line and the second fluid line facilitate the heat transfer between a heat exchanger of the refrigerant condenser and the one or more shelves when a first fluid flows through the first fluid flow path and a second fluid flows through second fluid flow path.

5. The freeze-drying system of claim 3, wherein the first fluid line defines the third fluid flow path that bypasses the heat exchanger when the first valve is closed and when the second valve is open.

6. The freeze-drying system of claim 3, further comprising:
    a flow controller, wherein the flow controller is to regulate fluid flow through the first fluid line and the second fluid line.

7. The freeze-drying system of claim 6, further comprising:
    a plurality of temperature sensing elements distributed throughout the first fluid line and the second fluid line.

8. The freeze-drying system of claim 6, wherein the flow controller is operatively coupled to the plurality of temperature sensors, and wherein the flow controller is to control the first valve and the second valve based on temperature measurements received from the plurality of temperature sensors.

9. The freeze-drying system of claim 7, wherein flow controller is to modulate the first valve to open and the second valve to close, or to modulate the first valve to close and the second valve to open, in response to determining that a temperature measurement satisfies a temperature threshold condition.

10. A method for energy recovery in a freeze-drying system, the method comprising:
    causing, by a processing device of the freeze-drying system, a first fluid to flow through a first fluid flow path of a first fluid line that passes through a refrigerant condenser and a heat exchanger of the freeze-drying system, wherein the first fluid line is thermally coupled to the refrigerant condenser and the heat exchanger;
    causing, by the processing device, a second fluid to flow through a second fluid flow path of a second fluid line that passes through the heat exchanger and one or more shelves disposed within a chamber of the freeze-drying system, wherein the second fluid flow path passes through the one or more shelves and bypasses the heat exchanger, and wherein the second fluid line is thermally coupled to the one or more shelves;
    in response to a determination by the processing device that a freeze-drying process condition is satisfied, causing, by the processing device, the second fluid to flow through a third fluid flow path of the second fluid line, wherein the third fluid flow path passes through the one or more shelves and the heat exchanger, wherein flowing the second fluid through the third fluid flow path thermally couples the one or more shelves to the heat exchanger to facilitate transfer of refrigerant condenser-produced heat to the one or more shelves, wherein the determination that the freeze-drying process condition has been satisfied comprises a determination that:
        a temperature of the first fluid or the second fluid has reached a target temperature,
        the one or more shelves have reached a target temperature,
        a particular step in a process recipe has occurred, or a user of the freeze-drying system has entered a command to override the process recipe.

11. The method of claim 10, further comprising:
in response to a determination by the processing device that the freeze-drying process condition is no longer satisfied, causing, by the processing device, the second fluid to flow through the second fluid flow path of the second fluid line so as to fluidly uncouple the one or more shelves from the heat exchanger.

12. The method of claim 10, further comprising:
in response to a determination by the processing device that the one or more shelves have reached a target temperature, causing, by the processing device, the second fluid to flow through the second fluid flow path of the second fluid line so as to fluidly uncouple the one or more shelves from the heat exchanger.

13. The method of claim 10, wherein when the one or more shelves are thermally coupled to the heat exchanger, heat from the refrigerant condenser is transferred to the one or more shelves.

14. The method of claim 10, further comprising:
measuring the temperature of the first fluid, wherein the freeze-drying process condition comprises determining, by the processing device, that the temperature of the first fluid has reached the target temperature.

15. The method of claim 14, wherein the target temperature corresponds to a temperature that is greater than that of the second fluid.

16. The method of claim 10, wherein causing the second fluid to flow through the third fluid flow path comprises opening a first valve and closing a second valve to divert the second fluid through the third fluid flow path.

17. A method for energy recovery in a freeze-drying system, the method comprising:
causing, by a processing device of the freeze-drying system, a first fluid to flow through a first fluid flow path of a first fluid line that passes through a heat exchanger and one or more shelves disposed within a chamber of a freeze-drying system, wherein the first fluid line is thermally coupled to the one or more shelves and the heat exchanger;
causing, by the processing device, a second fluid to flow through a second fluid flow path of a second fluid line that passes through the heat exchanger and a refrigerant condenser of the freeze-drying system, wherein the second fluid flow path passes through the refrigerant condenser and bypasses the heat exchanger, and wherein the second fluid line is thermally coupled to the refrigerant condenser;
in response to a determination by the processing device that a freeze-drying process condition is satisfied, causing, by the processing device, the second fluid to flow through a third fluid flow path of the second fluid line, wherein the third fluid flow path passes through the refrigerant condenser and the heat exchanger, wherein flowing the second fluid through the third fluid flow path thermally couples the refrigerant condenser to the heat exchanger to facilitate transfer of refrigerant condenser-produced heat to the one or more shelves, wherein the determination that the freeze-drying process condition has been satisfied comprises a determination that:
a temperature of the first fluid or the second fluid has reached a target temperature,
the one or more shelves have reached a target temperature,
a particular step in a process recipe has occurred, or
a user of the freeze-drying system has entered a command to override the process recipe.

18. The method of claim 17, further comprising:
in response to a determination by the processing device that the freeze-drying process condition is no longer satisfied, causing, by the processing device, the second fluid to flow through the second fluid flow path of the second fluid line so as to fluidly uncouple the refrigerant condenser from the heat exchanger.

* * * * *